US012570731B2

(12) United States Patent
Liang et al.

(10) Patent No.: US 12,570,731 B2
(45) Date of Patent: Mar. 10, 2026

(54) METHODS FOR TREATING CANCER WITH AN ANTI-APO B100 ANTIBODY

(71) Applicant: Abcentra, LLC, Los Angeles, CA (US)

(72) Inventors: Bertrand C. Liang, San Diego, CA (US); Stacey Ruiz, Beverly Hills, CA (US); Christopher John Farina, Los Angeles, CA (US)

(73) Assignee: Abcentra, LLC, Los Angeles, CA (US)

( * ) Notice: Subject to any disclaimer, the term of this patent is extended or adjusted under 35 U.S.C. 154(b) by 950 days.

(21) Appl. No.: 17/776,006

(22) PCT Filed: Nov. 12, 2020

(86) PCT No.: PCT/US2020/060309
§ 371 (c)(1),
(2) Date: May 11, 2022

(87) PCT Pub. No.: WO2021/097146
PCT Pub. Date: May 20, 2021

(65) Prior Publication Data
US 2022/0403013 A1      Dec. 22, 2022

Related U.S. Application Data

(60) Provisional application No. 62/934,078, filed on Nov. 12, 2019.

(51) Int. Cl.
| | |
|---|---|
| *C07K 16/18* | (2006.01) |
| *A61K 39/395* | (2006.01) |
| *A61K 45/06* | (2006.01) |
| *A61P 35/00* | (2006.01) |

(52) U.S. Cl.
CPC .......... *C07K 16/18* (2013.01); *A61K 39/3955* (2013.01); *A61K 45/06* (2013.01); *A61P 35/00* (2018.01); *C07K 2317/21* (2013.01)

(58) Field of Classification Search
None
See application file for complete search history.

(56) References Cited

U.S. PATENT DOCUMENTS

| | | |
|---|---|---|
| 2008/0199475 A1 | 8/2008 | Vollmers |
| 2009/0169544 A1 | 7/2009 | Nilsson et al. |
| 2009/0208503 A1 | 8/2009 | Carlsson et al. |
| 2009/0311271 A1 | 12/2009 | Harnish et al. |
| 2010/0239567 A1 | 9/2010 | Esue |

| | | |
|---|---|---|
| 2010/0286025 A1 | 11/2010 | Anantharamaiah et al. |
| 2013/0101588 A1 | 4/2013 | Vollmers |
| 2013/0243784 A1 | 9/2013 | Swergold |
| 2013/0253174 A1 | 9/2013 | Chiba et al. |
| 2017/0340702 A1 | 11/2017 | Carvlin et al. |
| 2018/0372749 A1 | 12/2018 | Watnick |
| 2019/0284268 A1 | 9/2019 | Nilsson et al. |

FOREIGN PATENT DOCUMENTS

| | | | |
|---|---|---|---|
| WO | WO-2004/030607 A2 | 4/2004 | |
| WO | WO-2010088739 A1 * | 8/2010 | .............. A61P 35/00 |
| WO | WO-2010/102241 A1 | 9/2010 | |
| WO | WO-2011/160845 A2 | 12/2011 | |
| WO | WO-2018/195283 A1 | 10/2018 | |
| WO | WO-2019/210207 A2 | 10/2019 | |
| WO | WO-2019/232070 A1 | 12/2019 | |

OTHER PUBLICATIONS

Moghadam et al (Biorganic & Medicinal Chemistry Letters, 2024, 106:129762, internet pp. 1-9).*
Deng et al (Frontiers in Oncology, 2022, 12:article 803473, internet pp. 1-17).*
Bitorina et al (BBA—Molecular and Cell Biology of Lipids, 2019, 1864:158518, internet pp. 1-9).*
Yan et al (Oncotarget, 2016, 7:24792-24799).*
Gazzaniga et al (Journal of Investigative Dermatology, 2007, 127:2031-2041).*
Wang et al (Oncology Letters, 2022, 23:1-9).*
Zubair et al (Current Allergy Asthma Rep. 2013; 13:44-49).*
Khurana et al (Cancers, 2020, 12; 2675; internet pp. 1-21).*
Chen et al (Oncogene, 2019, 39:1634-1651).*
González-Chavarría et al., "LOX-1 activation by oxLDL triggers an epithelial mesenchymal transition and promotes tumorigenic potential in prostate cancer cells," Cancer Lett. 414:34-43 (2018) (11 pages).
International Search Report and Written Opinion for International Application No. PCT/US2020/060309, mailed Feb. 17, 2021 (10 pages).
Bitorina et al., "Low profile high value target: The role of OxLDL in cancer," Biochim Biophys Acta Mol Cell Biol Lipids. 1864(12):158518 (Available online Aug. 31, 2019) (9 pages).
Kim et al., "Targeting ligand-receptor interactions for development of cancer therapeutics," Curr Opin Chem Biol. 38:62-69 (Jun. 2017).

* cited by examiner

*Primary Examiner* — Laura B Goddard
(74) *Attorney, Agent, or Firm* — Clark & Elbing LLP

(57) ABSTRACT

The present invention provides compositions and methods for treating cancer in a subject by administering to the subject an antibody or fragment thereof that binds to oxidized LDL. In some embodiments, the compositions and methods may reduce the size of the tumor, reduce macrophage infiltration, and/or inhibit metastasis.

18 Claims, 6 Drawing Sheets
Specification includes a Sequence Listing.

METHODS FOR TREATING CANCER WITH AN ANTI-APO B100 ANTIBODY

SEQUENCE LISTING

The instant application contains a Sequence Listing which has been submitted electronically in ASCII format and is hereby incorporated by reference in its entirety. Said ASCII copy, created on May 10, 2022, is named 51473-006002_Sequence_Listing_5_10_22_ST25 and is 12,656 bytes in size.

FIELD OF THE INVENTION

The invention generally relates to compositions and methods for treating cancer by inhibiting the biological activity of oxidized low-density lipoprotein.

BACKGROUND OF THE INVENTION

Obesity is believed to increase the risk for developing diabetes and several types of cancers. Obesity is linked to a variety of deleterious physiological changes including, for example, adipose tissue dysfunction, low-grade and chronic inflammation, and alterations in lipid metabolism and circulating hormone levels. Oxidized low-density lipoprotein (oxLDL) is a proinflammatory mediator that is formed as a result of oxidative modification of LDL in the arterial wall. OxLDL is most commonly associated with the development of atherosclerosis, which can have detrimental cardiovascular (CV) outcomes, including myocardial infarction, stroke, and death. OxLDL signals through various cellular scavenger receptors, including A-type scavenger receptors (SR-A), cluster of differentiation 36 (CD36), CD68, mucin, and lectin-like oxLDL receptor-1 (LOX-1).

LOX-1 is expressed on endothelial cells, but is also found on macrophages, smooth muscle cells, fibroblasts, and platelets. Additionally, LOX-1 is secreted in soluble form. Several studies have shown that oxLDL signaling through LOX-1 plays a major role in atherosclerosis development and progression. The present invention provides methods and compositions for treating cancer using an oxLDL-dependent mechanism.

SUMMARY OF THE INVENTION

In one aspect, the inventions provides methods for inhibiting macrophage infiltration into a tumor in a subject comprising administering to the subject a therapeutically effective amount of an antibody or fragment thereof that binds to oxidized low density lipoprotein (oxLDL) (i.e., an anti-oxLDL antibody or fragment thereof).

In another aspect, the invention provides methods for inhibiting metastasis of a tumor in a subject comprising administering to the subject a therapeutically effective amount of an antibody or fragment thereof that binds to oxidized low density lipoprotein (oxLDL) (i.e., an anti-oxLDL antibody or fragment thereof).

In some embodiments, the subject is diagnosed as having a tumor.

In some embodiments, the tumor is a LOX-1-positive tumor. In other embodiments, the tumor is positive for one or more of LOX-1, SR-A, CD36, CD38, and mucin.

In some embodiments, the tumor is selected from the group consisting of ovarian carcinoma, bladder urothelial carcinoma, kidney renal clear cell carcinoma, rectum adenocarcinoma, colon adenocarcinoma, prostate adenocarcinoma, a mammary epithelial cell tumor, a glioblastoma, pancreatic cancer, and esophageal cancer.

In some embodiments, the method reduces the growth rate of the tumor, macrophage infiltration of the tumor, and/or the metastatic potential of the tumor.

In another aspect, the invention provides a method for treating a cancer in a subject comprising administering to the subject a therapeutically effective amount of an antibody or fragment thereof that binds to oxidized low density lipoprotein (oxLDL).

In another aspect, the invention provides a method for treating a cancer in a subject comprising administering to the subject:

(a) a therapeutically effective amount of a primary anti-cancer therapy selected from the group consisting of a chemotherapy, radiation therapy, and immunotherapy, and (b) a therapeutically effective amount of an antibody or fragment thereof that binds to oxidized low density lipoprotein (oxLDL).

In some embodiments, the cancer is LOX-1-positive. In other embodiments, the cancer is positive for one or more of LOX-1, SR-A, CD36, CD38, and mucin.

In some embodiments, the cancer is selected from the group consisting of ovarian carcinoma, bladder urothelial carcinoma, kidney renal clear cell carcinoma, rectum adenocarcinoma, colon adenocarcinoma, prostate adenocarcinoma, a mammary epithelial cell tumor, a glioblastoma, pancreatic cancer, and esophageal cancer.

In some embodiments, the cancer is a hematological cancer including, for example, acute lymphoblastic leukemia, acute myelogenous leukemia, chronic lymphocytic leukemia, chronic myelogenous leukemia, acute monocytic leukemia, Non-Hodgkin's lymphoma, and multiple myeloma.

In some embodiments, the antibody or fragment thereof is administered as an adjuvant to the primary anticancer therapy.

In some embodiments, the subject is diagnosed as having serum hyperlipidemia, type 2 diabetes, or metabolic syndrome.

In some embodiments of any of the foregoing aspects, the anti-oxLDL antibody or fragment thereof inhibits binding of oxLDL to LOX-1. In other embodiments, the antibody or fragment thereof inhibits binding of oxLDL to one or more of SR-A, CD36, CD38, and mucin.

In some embodiments of any of the foregoing aspects, the antibody or fragment thereof binds to oxLDL with at least 10-times, 50-times, 100-times, or 1,000-times greater affinity than for native (unoxidized) LDL.

In some embodiments, the antibody is a human antibody, a humanized antibody, a murine antibody, or a rabbit antibody, or a fragment thereof.

In some embodiments, the antibody or fragment thereof comprises at least one light chain complementarity determining region (LCDR) that is substantially identical to an LCDR selected from the group consisting of SEQ ID NO: 8, SEQ ID NO: 9, and SEQ ID NO: 10.

In some embodiments, the antibody or fragment thereof comprises at least one heavy chain complementarity determining region (HCDR) that is substantially identical to an LCDR selected from the group consisting of SEQ ID NO: 5, SEQ ID NO: 6, and SEQ ID NO: 7.

In some embodiments, the antibody or fragment thereof comprises a variable heavy region ($V_H$) that is substantially identical to SEQ ID NO: 11, a variable light region ($V_L$) that is substantially identical to SEQ ID NO: 12, or both In some embodiments, the antibody or fragment thereof comprises a heavy chain that is substantially identical to (SEQ ID NO: 3)
EVQLLESGGGLVQPGGSLRLSCAASGFTFSNAWMSWVRQAPGKGLEWVSS

ISVGGHRTYYADSVKGRSTISRDNSKNTLYLQMNSLRAEDTAVYYCARIR

VGPSGGAFDYWGQGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPG

K, a light chain that is substantially identical to (SEQ ID NO: 4)
QSVLTQPPSASGTPGQRVTISCSGSNTNIGKNYVSWYQQLPGTAPKLLIY

ANSNRPSGVPDRFSGSKSGTSASLAISGLRSEDEADYYCASWDASLNGWV

FGGGTKLTVLGQPKAAPSVTLFPPSSEELQANKATLVCLISDFYPGAVTV

AWKADSSPVKAGVETTTPSKQSNNKYAASSYLSLTPEQWKSHRSYSCQVT

HEGSTVEKTVAPTECS, or both.

The heavy chain may be encoded by a polynucleotide sequence substantially identical to (SEQ ID NO: 1)
gaggtgcagctgttggagtctggggggaggcttggtacagcctggggggtc cctgagactctcctgtgcagcctctggattcaccttcagtaacgcctgga tgagctgggtccgccaggctccagggaaggggctggagtgggtctcaagt attagtgttggtggacataggacatattatgcagattccgtgaagggccg gtccaccatctccagagacaattccaagaacacgctgtatctgcaaatga acagcctgagagccgaggacactgccgtgtattactgtgcacggatacgg gtgggtccgtccggcggggcctttgactactggggccagggtacactggt caccgtgagctcagcctccaccaagggcccatcggtcttccccctggcac cctcctccaagagcacctctgggggcacagcggccctgggctgcctggtc aaggactacttccccgaaccggtgacggtgtcgtggaactcaggcgcccc tgaccagcggcgtgcacaccttcccggctgtcctacagtcctcaggactc tactccctcagcagcgtggtgaccgtgccctccagcagcttgggcaccca gacctacatctgcaacgtgaatcacaagcccagcaacaccaaggtggaca agaaagttgagcccaaatcttgtgacaaaactcacacatgcccaccgtgc ccagcacctgaactcctggggggaccgtcagtcttcctcttcccccaaa acccaaggacaccctcatgatctcccggacccctgaggtcacatgcgtgg tggtggacgtgagccacgaagaccctgaggtcaagttcaactggtacgtg gacggcgtggaggtgcataatgccaagacaaagccgcgggaggagcagta -continued caacagcacgtaccgtgtggtcagcgtcctcaccgtcctgcaccaggact ggctgaatggcaaggagtacaagtgcaaggtctccaacaaagccctccca gcccccatcgagaaaaccatctccaaagccaaagggcagccccgagaacc acaggtgtacaccctgcccccatcccgggatgagctgaccaagaaccagg tcagcctgacctgcctggtcaaaggcttctatcccagcgacatcgccgtg gagtgggagagcaatgggcagccggagaacaactacaagaccacgcctcc cgtgctggactccgacggctccttcttcctctacagcaagctcaccgtgg acaagagcaggtggcagcaggggaacgtcttctcatgctccgtgatgcat gaggctctgcacaaccactacacgcagaagagcctctccctgtctccggg taaa, and the light chain may be encoded by a polynucleotide sequence substantially identical to (SEQ ID NO: 2)
cagtctgtgctgactcagccaccctcagcgtctgggaccccgggcagag ggtcaccatctcctgctctggaagcaacaccaacattgggaagaactatg tatcttggtatcagcagctcccaggaacggcccccaaactcctcatctat gctaatagcaatcggccctcagggggtccctgaccgattctctggctccaa gtctggcacctcagcctccctggccatcagtgggctccggtccgaggatg aggctgattattactgtgcgtcatgggatgccagcctgaatggttgggta ttcggcggaggaaccaagctgacggtcctaggtcagcccaaggctgcccc ctcggtcactctgttcccgccctcctctgaggagcttcaagccaacaagg ccacactggtgtgtctcataagtgacttctacccgggagccgtgacagtg gcctggaaggcagatagcagccccgtcaaggcgggagtggagaccaccac accctccaaacaaagcaacaacaagtacgcggccagcagctatctgagcc tgacgcctgagcagtggaagtcccacagaagctacagctgccaggtcacg catgaagggagcaccgtggagaagacagtggcccctacagaatgttca.

In some embodiments, the antibody is orticumab. In other embodiments, the antibody fragment is a fragment of orticumab.

In some embodiments, the antibody is administered intravenously at an initial dose of at least 5 mg/kg, followed by a plurality of subsequent doses, each at least 2 mg/kg/week, at least 2.5 mg/kg/two weeks, or at least 6 mg/kg/month. In other embodiments, the antibody is administered subcutaneously at a dose of about 330 mg/month for at least three months.

"Adjuvant therapy" as used herein refers to a secondary therapy that is administered to treat the primary disease (i.e., the clinical indication against which the primary therapy is directed), a secondary disease requiring treatment, to increase/maximize the effectiveness of a primary therapy, to mitigate a side effect of therapy or the primary disease, and/or to prevent recurrence of the disease. In some embodiments, the antibody or antibody fragments are administered as an adjuvant to either treat the primary disease (e.g., a cancer or tumor) or to reduce the plasma concentration of oxLDL.

"Administering" and/or "administer" as used herein refer to any route for delivering a pharmaceutical composition to a patient. Routes of delivery may include non-invasive peroral (through the mouth), topical (skin), transmucosal (nasal, buccal/sublingual, vaginal, ocular and rectal) and inhalation routes, as well as parenteral routes, and other methods known in the art. Parenteral refers to a route of delivery that is generally associated with injection, including intraorbital, infusion, intraarterial, intracarotid, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

The term "effective amount" as used herein refers to the amount of a pharmaceutical composition to decrease at least one or more symptom of the disease or disorder and relates to a sufficient amount of pharmacological composition to provide the desired effect. The phrase "therapeutically effective amount" as used herein means a sufficient amount of the composition to treat a disorder, at a reasonable benefit/risk ratio applicable to any medical treatment.

A therapeutically or prophylactically significant reduction in a symptom is, e.g. at least about 10%, at least about 20%, at least about 30%, at least about 40%, at least about 50%, at least about 60%, at least about 70%, at least about 80%, at least about 90%, at least about 100%, at least about 125%, at least about 150% or more in a measured parameter as compared to a control or non-treated subject or the state of the subject prior to administering the peptides described herein. Measured or measurable parameters include clinically detectable markers of disease, for example, elevated or depressed levels of a biological marker, as well as parameters related to a clinically accepted scale of symptoms or markers for atherosclerosis. It will be understood, however, that the total daily usage of the compositions and formulations as disclosed herein will be decided by the attending physician within the scope of sound medical judgment. The exact amount required will vary depending on factors such as the type of disease being treated, gender, age, and weight of the subject.

"Subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. In certain embodiments, the mammal is a human subject.

By "substantially identical" is meant a nucleic acid or amino acid sequence that, when optimally aligned, for example using the methods described below, share at least 60%, 65%, 70%, 75%, 80%, 85%, 90%, 95%, 96%, 97%, 98%, 99%, or 100% sequence identity with a second nucleic acid or amino acid sequence. "Substantial identity" may be used to refer to various types and lengths of sequence, such as full-length sequence, epitopes or immunogenic peptides, functional domains, coding and/or regulatory sequences, exons, introns, promoters, and genomic sequences. Percent identity between two polypeptides or nucleic acid sequences is determined in various ways that are within the skill in the art, for instance, using publicly available computer software such as Smith Waterman Alignment (Smith, T. F. and M. S. Waterman (1981) J Mol Biol 147:195-7); "BestFit" (Smith and Waterman, Advances in Applied Mathematics, 482-489 (1981)) as incorporated into GeneMatcher Plus™, Schwarz and Dayhof (1979) Atlas of Protein Sequence and Structure, Dayhof, M. O., Ed pp 353-358; BLAST program (Basic Local Alignment Search Tool; (Altschul, S. F., W. Gish, et al. (1990) J Mol Biol 215: 403-10), BLAST-2, BLAST-P, BLAST-N, BLAST-X, WU-BLAST-2, ALIGN, ALIGN-2, CLUSTAL, or Megalign (DNASTAR) software. In addition, those skilled in the art can determine appropriate parameters for measuring alignment, including any algorithms needed to achieve maximal alignment over the length of the sequences being compared. In general, for proteins, the length of comparison sequences will be at least 10 amino acids, preferably 20, 30, 40, 50, 60, 70, 80, 90, 100, 110, 120, 130, 140, 150, 200, 250, 300, 350, or 400 amino acids or more. For nucleic acids, the length of comparison sequences will generally be at least 25, 50, 100, 125, 150, 200, 250, 300, 350, 400, 450, 500, 550, 600, 650, 700, 800, 900, 1000, 1100, or 1200 or more. It is understood that for the purposes of determining sequence identity when comparing a DNA sequence to an RNA sequence, a thymine nucleotide is equivalent to a uracil nucleotide. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

DESCRIPTION OF THE DRAWINGS

The present invention may be better understood by referring to the following figures. The components in the figures are not necessarily to scale, emphasis instead being placed upon illustrating the principles of the disclosure. In the figures, reference numerals designate corresponding parts throughout the different views.

DETAILED DESCRIPTION

Figure 1:
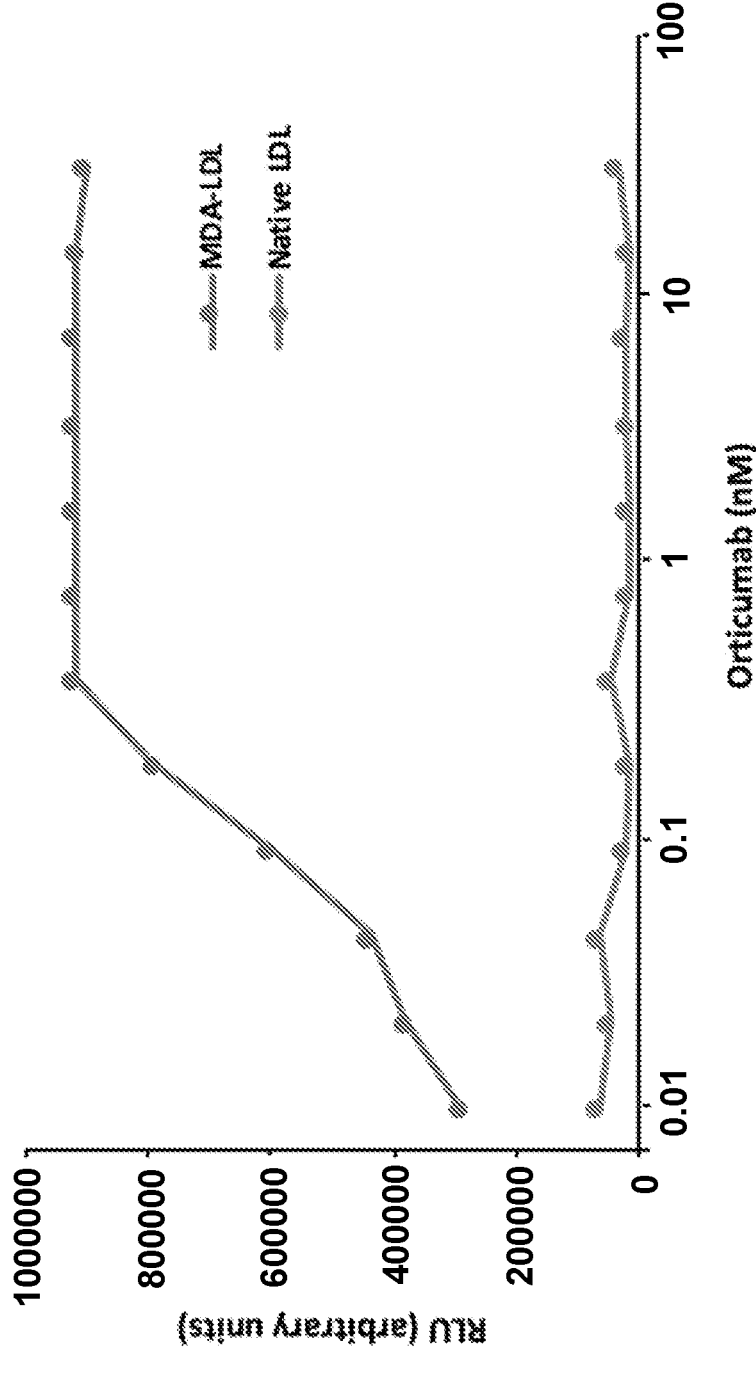
FIG. 1 is a line graph comparing orticumab binding to native (unoxidized) LDL and MDA-LDL.

It is well-accepted that fat-enriched diets and lipid-related diseases increase the incidence of certain types of cancer including breast, prostate, colon, and liver. Plasma lipids have been correlated with several types of cancer. In particular, total cholesterol (TC), triglycerides (TG), and LDL are found to be significantly higher in some breast cancer patients.

A high fat diet can induce a switch towards a favorable microenvironment that supports the development and growth of cancer cells. The switch is caused by changes in hormonal environment or the properties of cell membranes, the latter due to alterations in lipid composition, or by means of modulating immune responses to tumor cells. And as in other lipid-related metabolic diseases (e.g., obesity and NASH), oxidative stress results in oxidation of LDL to oxLDL which causes a plethora of pro-mutagenic and pro-carcinogenic effects. Various clinical studies underscore the role of oxLDL in the carcinogenic process and positive correlations between increased serum oxLDL concentration and cancer risk have been reported for pancreatic, colon, breast as well as esophageal cancer. Additionally, in a clinical study of colorectal cancer (CRC) patients, products of lipid oxidation as a consequence of oxidative stress, including oxLDL were studied as potential markers of CRC development. Although this study did not observe significant differences in oxLDL serum levels between CRC patients and healthy controls, levels of oxLDL were shown to be significantly higher in patients with an early stage of primary tumor compared to patients with advanced stage primary tumor progression (Diakowska et al, Gastroenterol. Res. Pract. 2015:146819 (2015)).

OxLDL-mediated signaling via LOX-1 causes an upregulation of adhesion proteins, other proinflammatory mediators, and proangiogenic factors, all of which are pathogenic in cancer. Among these pathogenic signaling molecules are monocyte chemoattractant protein-1 (MCP-1) and nuclear factor-kappa B (NFκB). MCP-1 is a chemokine that drives macrophage recruitment to areas of inflammation, and its expression correlates with the extent of tumor-associated-macrophage (TAM) infiltration. NFκB is a transcription factor that serves as the major regulator of pro-inflammatory gene expression. NFκB activity is upregulated in inflammatory conditions, including cancer, where it contributes to transformation of normal cells to tumor cells, tumor cell survival, and the ongoing inflammatory cycle perpetuated in cancer. Importantly, oxLDL-Lox-1-mediated signaling has been implicated in both MCP-1 upregulation and NFκB activity.

The present inventions are based, in part, on a characterization of anti-cancer properties of anti-oxLDL antibodies. Directly interfering with oxLDL can inhibit LOX-1-mediated tumorigenesis and/or progression. The present inventions also are based on the discovery that orticumab specifically binds the oxidized form of LDL (i.e., oxLDL) relative to the native/unoxidized LDL. Orticumab is a fully human recombinant monoclonal IgG1 antibody that has an affinity for oxLDL of about 8±6 nM.

Anti-oxLDL Antibodies

As discussed herein, the inventions incorporate anti-oxLDL antibodies. One particularly useful anti-oxLDL antibody is orticumab. The synthesis and characterization of orticumab is described in WO 2009/08205 and is referred to therein as antibody 2D03. WO 2009/08205 is hereby incorporated by reference in its entirety.

FIG. 2 of WO 2009/08205 describes the amino acid sequence of the 2D03 heavy chain and the 2D03 light chain, underlining the complementarity determining regions (CDRs).

WO 2007/025781, which is hereby incorporated by reference in its entirety, describes that its invention also includes an antibody that selectively binds to the oxidized-LDL epitope that is selectively bound by antibody 2D03 (i.e., orticumab) and further includes an antibody comprising at least one, two, three, four, five, or all six complementarity determining region(s) (CDRs) that has the amino acid sequence of the corresponding CDR of antibody 2D03. (See, for example, pages 16, 29, and 30.) Furthermore, an antibody with three or four CDRs having sequences corresponding to the 2D03 antibody CDRs preferably has all three heavy chain or all three light chain CDRs that have the sequence of the corresponding CDRs of antibody 2D03; that thus this aspect of the invention includes an antibody comprising three light chain CDRs that have the sequence of the corresponding three light chain CDRs of antibody 2D03, or three heavy chain CDRs that have the sequence of the corresponding three heavy chain CDRs of antibody 2D03; that yet more preferably, the antibody comprises three light chain CDRs and three heavy chain CDRs that have the sequence of the corresponding CDRs of antibody 2D03; that if the antibody does not comprise all six CDRs that have the sequence of the corresponding CDRs of antibody 2D03, it is preferred if some or all of the 1, 2, 3, 4 or 5 "non-identical" CDRs comprise a variant of the sequence of the corresponding CDRs of antibody 2D03, (by "a variant" WO 2007/025781 includes the meaning that the variant has at least 50% sequence identity with the sequence of the corresponding CDR, more preferably at least 70%, yet more preferably at least 80% or at least 90% or at least 95%; most preferably, the variant has 96% or 97% or 98% or 99% sequence identity with the sequence of the corresponding CDR of antibody 2D03; typically the "variant" CDR sequence has 5 or 4 or 3 or 2 or only 1 amino acid residue difference from the sequence of the corresponding CDR of antibody 2D03); and that this aspect of the invention includes antibody 2D03.

The heavy chain complementarity determining region (HCDR) 1 (HCDR1), 2 (HCDR2) and 3 (HCDR3) are set forth in SEQ ID Nos: 5, 6 and 7, respectively; and light chain complementarity determining regions (LCDR) 1 (LCDR1), 2 (LCDR2) and 3 (LCDR3) are set forth in SEQ ID Nos: 8, 9 and 10, respectively. Orticumab contains a variable heavy region (VH) amino acid sequence of SEQ ID No: 11, and a variable light region (VL) amino acid sequence of SEQ ID No: 12. Orticumab contains a heavy chain amino acid sequence of SEQ ID No: 3, a light chain amino acid sequence of SEQ ID No: 4.

```
HCDR1 is
                        (SEQ ID NO: 5)
FSNAWMSWVRQAPG.

HCDR2 is
                        (SEQ ID NO: 6)
SSISVGGHRTYYADSVKGR.

HCDR3 is
                        (SEQ ID NO: 7)
ARIRVGPSGGAFDY.

LCDR1 is
                        (SEQ ID NO: 3)
CSGSNTNIGKNYVS.

LCDR2 is
                        (SEQ ID NO: 9)
ANSNRPS.

LCDR3 is
                        (SEQ ID NO: 10)
CASWDASLNGWV.
```

Variable heavy region $(V_H)$ is:

```
                        (SEQ ID NO: 11)
EVQLLESGGG LVQPGGSLRL SCAASGFTPS NAWMSWVRQA

PGKGLEWVSS ISVGGHRTYY ADSVEGRSTI SRDNSKNTLY

LQMNSLRAED TAVYYCARIR VGPSGGAFDY WGQGTLVTVS.
```

Variable light region (V_L) is:

```
                                            (SEQ ID NO: 12)
QSVLTQPPSA SGTPGQRVTI SCSGSNTNIG KNYVSWYQQL

PGTAPKLLIY ANSNRPSGVP DRFSGSKSGT SASLAISGLR

SEDEADYYCA SWDASLNGWV FGGGTKLTVL.
```

In some embodiments, the antibodies or antibody fragments comprise, consist of, or consist essentially of the sequence set forth in SEQ ID NOs: 1 and/or 2.

In some embodiments, the invention provides an antibody or antibody fragment that binds to oxLDL and one or more of HCDR1, HCDR2, HCDR3, LCDR1, LCDR2 and LCDR3 as set forth in SEQ ID Nos.: 5-10, respectively.

In some embodiments, the invention provides an antibody comprising at least one CDR that has the amino acid sequence of the corresponding CDR of orticumab. More preferably, the antibody has two or three or four or five CDRs that have the sequence of the corresponding CDRs of orticumab. If the antibody has three or four CDRs that have the sequence of the corresponding CDRs of orticumab, it is preferred if the antibody has all three heavy chain or all three light chain CDRs that have the sequence of the corresponding CDRs of orticumab. Thus, this aspect of the methods includes an antibody comprising three light chain CDRs that have the sequence of the corresponding three light chain CDRs of orticumab, or three heavy chain CDRs that have the sequence of the corresponding three heavy chain CDRs of orticumab. Yet more preferably, the antibody comprises three light chain CDRs and three heavy chain CDRs that have the sequence of the corresponding CDRs of orticumab.

If the antibody does not comprise all six CDRs that have the sequence of the corresponding CDRs of orticumab, it is preferred if some or all of the 1, 2, 3, 4 or 5 "non-identical" CDRs comprise a variant of the sequence of the corresponding CDRs of orticumab. By "a variant," we include the meaning that the variant has at least 50% sequence identity with the sequence of the corresponding CDR, more preferably at least 70%, yet more preferably at least 80% or at least 90% or at least 95%. Most preferably, the variant has 96% or 97% or 98% or 99% sequence identity with the sequence of the corresponding CDR of orticumab. Typically, the "variant" CDR sequence has 5 or 4 or 3 or 2 or only 1 amino acid residue difference from the sequence of the corresponding CDR of orticumab.

In particular, the invention provides an antibody containing "one or more of HCDR1, HCDR2, HCDR3, LCDR1, LCDR2 and LCDR3" encompasses embodiments that the antibody contains one, any two, any three, any four, any five or all six of the CDRs (i.e., HCDR1, HCDR2, HCDR3, LCDR1, LCDR2 and LCDR3). For example, one aspect of the embodiment provides that the antibody contains HCDR1 as set forth in SEQ ID NO: 5. Another aspect provides that the antibody contains HCDR2 as set forth in SEQ ID NO: 6. Another aspect provides that the antibody contains HCDR3 as set forth in SEQ ID NO: 7. Yet another aspect provides that the antibody contains LCDR1 as set forth in SEQ ID NO: 8. Another aspect provides that the antibody contains LCDR2 as set forth in SEQ ID NO: 9. Another aspect provides that the antibody contains LCDR3 as set forth in SEQ ID NO:10. Yet another aspect provides that the antibody contains HCDR1 as set forth in SEQ ID NO:5 and HCDR2 as set forth in SEQ ID NO: 6. Another aspect provides that the antibody contains HCDR1 as set forth in SEQ ID NO:5 and HCDR3 as set forth in SEQ ID NO: 7.

Another aspect provides that the antibody contains HCDR1 as set forth in SEQ ID NO:5 and LCDR1 as set forth in SEQ ID NO: 8. Another aspect provides that the antibody contains HCDR1 as set forth in SEQ ID NO:5 and LCDR2 as set forth in SEQ ID NO: 9. Another aspect provides that the antibody contains HCDR1 as set forth in SEQ ID NO:5 and LCDR3 as set forth in SEQ ID NO: 10. Another aspect provides that the antibody contains HCDR2 as set forth in SEQ ID NO:6 and HCDR3 as set forth in SEQ ID NO: 7. Another aspect provides that the antibody contains HCDR2 as set forth in SEQ ID NO:6 and LCDR1 as set forth in SEQ ID NO: 8 Another aspect provides that the antibody contains HCDR2 as set forth in SEQ ID NO:6 and LCDR2 as set forth in SEQ ID NO: 9. Another aspect provides that the antibody contains HCDR2 as set forth in SEQ ID NO:6 and LCDR3 as set forth in SEQ ID NO: 10. Another aspect provides that the antibody contains HCDR3 as set forth in SEQ ID NO:7 and LCDR1 as set forth in SEQ ID NO: 8. Another aspect provides that the antibody contains HCDR3 as set forth in SEQ ID NO:7 and LCDR2 as set forth in SEQ ID NO: 9. Another aspect provides that the antibody contains HCDR3 as set forth in SEQ ID NO:7 and LCDR3 as set forth in SEQ ID NO: 10. Another aspect provides that the antibody contains LCDR1 as set forth in SEQ ID NO:8 and LCDR2 as set forth in SEQ ID NO: 9. Another aspect provides that the antibody contains LCDR1 as set forth in SEQ ID NO:8 and LCDR3 as set forth in SEQ ID NO: 10. Another aspect provides that the antibody contains LCDR2 as set forth in SEQ ID NO:9 and LCDR3 as set forth in SEQ ID NO: 10. Another aspect provides that the antibody contains HCDR1, HCDR2 and HCDR3 as set forth in SEQ ID NOs.: 5-7, respectively. Another aspect provides that the antibody contains HCDR1, HCDR2 and LCDR1 as set forth in SEQ ID NOs.: 5, 6 and 8, respectively. Another aspect provides that the antibody contains HCDR1, HCDR2 and LCDR2 as set forth in SEQ ID NOs.: 5, 6 and 9, respectively. Another aspect provides that the antibody contains HCDR1, HCDR2 and LCDR3 as set forth in SEQ ID NOs.: 5, 6 and 10, respectively. Another aspect provides that the antibody contains HCDR1, HCDR3 and LCDR1 as set forth in SEQ ID NOs.: 5, 7 and 8, respectively. Another aspect provides that the antibody contains HCDR1, HCDR3 and LCDR2 as set forth in SEQ ID NOs.: 5, 7 and 9, respectively. Another aspect provides that the antibody contains HCDR1, HCDR3 and LCDR3 as set forth in SEQ ID NOs.: 5, 7 and 10, respectively. Another aspect provides that the antibody contains HCDR1, LCDR1 and LCDR2 as set forth in SEQ ID NOs.: 5, 9 and 10, respectively. Another aspect provides that the antibody contains HCDR1, LCDR1 and LCDR3 as set forth in SEQ ID NOs.: 5, 8 and 10, respectively. Another aspect provides that the antibody contains HCDR1, LCDR2 and LCDR3 as set forth in SEQ ID NOs.: 5, 9 and 10, respectively. Another aspect provides that the antibody contains HCDR2, HCDR3 and LCDR1 as set forth in SEQ ID NOs.: 6, 7 and 8, respectively. Another aspect provides that the antibody contains HCDR2, HCDR3 and LCDR2 as set forth in SEQ ID NOs.: 6, 7 and 9, respectively. Another aspect provides that the antibody contains HCDR2, HCDR3 and LCDR3 as set forth in SEQ ID NOs.: 6, 7 and 10, respectively. Another aspect provides that the antibody contains HCDR2, LCDR1 and LCDR2 as set forth in SEQ ID NOs.: 6, 8 and 10, respectively. Another aspect provides that the antibody contains HCDR2, LCDR1 and LCDR3 as set forth in SEQ ID NOs.: 6, 8 and 10, respectively. Another aspect provides that the antibody contains HCDR2, LCDR2 and LCDR3 as set forth in SEQ ID NOs.: 6, 9 and 10, respectively. Another aspect provides that the antibody contains HCDR3, LCDR1 and LCDR2 as set forth in SEQ ID NOs.: 7, 8 and 9, respectively. Another aspect provides that the antibody contains HCDR3, LCDR1 and LCDR3 as set forth in SEQ ID NOs.: 7, 8 and 10, respectively. Another aspect provides that the antibody contains HCDR3, LCDR2 and LCDR3 as set forth in SEQ ID NOs.: 7, 9 and 10, respectively. Another aspect provides that the antibody contains LCDR1, LCDR2 and LCDR3 as set forth in SEQ ID NOs.: 8-10, respectively. Yet another aspect provides that the antibody contains HCDR1, HCDR2, HCDR3 and LCDR1 as set forth in SEQ ID NOs.: 5-8, respectively. Another aspect provides that the antibody contains HCDR1, HCDR2, HCDR3 and LCDR2 as set forth in SEQ ID NOs.: 5-7 and 10, respectively. Another aspect provides that the antibody contains HCDR1, HCDR2, HCDR3 and LCDR3 as set forth in SEQ ID NOs.: 5-7 and 10, respectively. Another aspect provides that the antibody contains HCDR1, HCDR2, LCDR1 and LCDR2 as set forth in SEQ ID NOs.: 5, 6, 8 and 9, respectively. Another aspect provides that the antibody contains HCDR1, HCDR2, LCDR1 and LCDR3 as set forth in SEQ ID NOs.: 5, 6, 8 and 10, respectively. Another aspect provides that the antibody contains HCDR1, HCDR2, LCDR2 and LCDR3 as set forth in SEQ ID NOs.: 5, 6, 9 and 10, respectively. Another aspect provides that the antibody contains HCDR1, HCDR3, LCDR1 and LCDR2 as set forth in SEQ ID NOs.: 5, 7, 8 and 9, respectively. Another aspect provides that the antibody contains HCDR1, HCDR3, LCDR1 and LCDR3 as set forth in SEQ ID NOs.: 5, 7, 8 and 10, respectively. Another aspect provides that the antibody contains HCDR1, HCDR3, LCDR2 and LCDR3 as set forth in SEQ ID NOs.: 5, 7, 9 and 10, respectively. Another aspect provides that the antibody contains HCDR1, LCDR1, LCDR2 and LCDR3 as set forth in SEQ ID NOs.: 5, 8, 9 and 10, respectively. Another aspect provides that the antibody contains HCDR2, HCDR3, LCDR1 and LCDR2 as set forth in SEQ ID NOs.: 6-9, respectively. Another aspect provides that the antibody contains HCDR2, HCDR3, LCDR1 and LCDR3 as set forth in SEQ ID NOs.: 6-8 and 10, respectively. Another aspect provides that the antibody contains HCDR2, HCDR3, LCDR2 and LCDR3 as set forth in SEQ ID NOs.: 6, 7, 9 and 10, respectively. Another aspect provides that the antibody contains HCDR2, LCDR1, LCDR2 and LCDR3 as set forth in SEQ ID NOs.: 6, 8, 9 and 10, respectively. Another aspect provides that the antibody contains HCDR3, LCDR1, LCDR2 and LCDR3 as set forth in SEQ ID NOs.: 7-10, respectively. Yet another aspect provides that the antibody contains HCDR1, HCDR2, HCDR3, LCDR1 and LCDR2 as set forth in SEQ ID NOs.: 5-9 respectively. Another aspect provides that the antibody contains HCDR1, HCDR2, HCDR3, LCDR1 and LCDR3 as set forth in SEQ ID NOs.: 5-8 and 10 respectively. Another aspect provides that the antibody contains HCDR1, HCDR2, HCDR3, LCDR2 and LCDR3 as set forth in SEQ ID NOs.: 5-7, 9 and 10 respectively. Another aspect provides that the antibody contains HCDR1, HCDR2, LCDR1, LCDR2 and LCDR3 as set forth in SEQ ID NOs.: 5, 6, 8-10, respectively. Another aspect provides that the antibody contains HCDR1, HCDR3, LCDR1, LCDR2 and LCDR3 as set forth in SEQ ID NOs.: 5, 7-10, respectively. Another aspect provides that the antibody contains HCDR2, HCDR3, LCDR1, LCDR2 and LCDR3 as set forth in SEQ ID NOs.: 6-10, respectively. Yet another aspect provides that the antibody contains HCDR1, HCDR2, HCDR3, LCDR1, LCDR2 and LCDR3 as set forth in SEQ ID NOs.: 5-10, respectively.

When making and using variants of any of the polypeptide sequences (e.g., CDRs) provided herein, it is understood that a given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics or substitutions of residues with similar side chain volume are well known. Isolated antibodies comprising conservative amino acid substitutions can be tested in any one of the assays described herein to confirm that a desired activity, as determined by the assays described elsewhere herein.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile, Phe, Trp; (2) neutral hydrophilic: Cys, Ser, Thr, Asn, Gln, Ala, Tyr, His, Pro, Gly; (3) acidic: Asp, Glu; (4) basic: His, Lys, Arg; (5) residues that influence chain orientation: Gly, Pro; (6) aromatic: Trp, Tyr, Phe, Pro, His, or hydroxyproline. Non-conservative substitutions will entail exchanging a member of one of these classes for another class.

Particularly preferred conservative substitutions for use in the variants described herein are as follows: Ala into Gly or into Ser; Arg into Lys; Asn into Gln or into His; Asp into Glu or into Asn; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr or into Phe; Tyr into Phe or into Trp; and/or Phe into Val, into Tyr, into Ile or into Leu. In general, conservative substitutions encompass residue exchanges with those of similar physicochemical properties (i.e. substitution of a hydrophobic residue for another hydrophobic amino acid).

Any cysteine residue not involved in maintaining the proper conformation of the isolated peptide as described herein can also be substituted, generally with serine, to improve the oxidative stability of the molecule and prevent aberrant crosslinking. Conversely, cysteine bond(s) can be added to the isolated peptide as described herein to improve its stability or facilitate multimerization.

In some embodiments, an antibody as described herein can comprise naturally occurring amino acids commonly found in polypeptides and/or proteins produced by living organisms, e.g. Ala (A), Val (V), Leu (L), Ile (I), Pro (P), Phe (F), Trp (W), Met (M), Gly (G), Ser (S), Thr (T), Cys (C), Tyr (Y), Asn (N), Gln (Q), Asp (D), Glu (E), Lys (K), Arg (R), and His (H). In some embodiments, the antibody can comprise alternative amino acids. Non-limiting examples of alternative amino acids include, D-amino acids; beta-amino acids; homocysteine, phosphoserine, phosphothreonine, phosphotyrosine, hydroxyproline, gamma-carboxyglutamate; hippuric acid, octahydroindole-2-carboxylic acid, statine, 1,2,3,4-tetrahydroisoquinoline-3-carboxylic acid, penicillamine (3-mercapto-D-valine), ornithine, citruline, alpha-methyl-alanine, para-benzoylphenylalanine, para-amino phenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, trifluorovaline; hexafluoroleucine; fluorinated analogs; azide-modified amino acids; alkyne-modified amino acids; cyano-modified amino acids; and derivatives thereof.

In some embodiments, an antibody can be modified, e.g. a moiety can be added to one or more of the amino acids. In some embodiments, the antibody can comprise one or more moiety molecules, e.g. 1 or more moiety molecules per peptide, 2 or more moiety molecules per peptide, 5 or more moiety molecules per peptide, 10 or more moiety molecules per antibody or more moiety molecules per antibody. In some embodiments, an antibody as described herein can comprise one more types of modifications and/or moieties, e.g. 1 type of modification, 2 types of modifications, 3 types of modifications or more types of modifications. Non-limiting examples of modifications and/or moieties include PEGylation; glycosylation; HESylation; ELPylation; lipidation; acetylation; amidation; end-capping modifications; cyano groups; phosphorylation; and cyclization. In some embodiments, an end-capping modification can comprise acetylation at the N-terminus, N-terminal acylation, and N-terminal formylation. In some embodiments, an end-capping modification can comprise amidation at the C-terminus, introduction of C-terminal alcohol, aldehyde, ester, and thioester moieties.

Therapeutic Methods

The invention also provides methods for treating or prevent a cancer by administering to a subject a therapeutically-effective amount of an antibody or antibody fragment that specifically binds to oxLDL. The invention also provides methods for preventing metastasis in a subject diagnosed as having a cancer by administering to a subject a therapeutically-effective amount of an antibody or antibody fragment that specifically binds to oxLDL. In some embodiments, binding of the antibody or antibody fragment inhibits or blocks at least one biological function of oxLDL. In some embodiments, the cancer is pancreatic cancer, breast cancer, colorectal cancer including rectal adenocarcinoma and colon adenocarcinoma, ovarian cancer, bladder urothelial carcinoma, kidney renal clear cell carcinoma, prostate cancer (prostate adenocarcinoma), In some embodiments, the cancer cells express and/or are identified as expressing LOX-1. In some embodiments, the antibody or antibody fragment inhibits, reduces, or blocks the binding of oxLDL to LOX-1. In some embodiments, the antibody or antibody fragment inhibits, reduces, or blocks the binding of oxLDL to SR-A, CD36, CD38, and/or mucin. In some embodiments, the antibody or antibody fragment is orticumab, a fragment of orticumab, a derivative of orticumab, or any anti-oxLDL antibody or antibody fragment described herein.

In various embodiments, the composition to be administered in the disclosed methods are formulated for delivery via any route of administration. For example, the methods include administration via an aerosol, nasal, oral, transmucosal, transdermal, parenteral or enteral route. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the parenteral route, the compositions may be in the form of solutions or suspensions for infusion or for injection. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Typically, the compositions are administered by injection.

Typically, an effective amount of the anti-oxLDL in the methods disclosed herein, results in a plasma concentration of at least 4 μg/mL, preferably at least 12 μg/mL in the subject.

The inventive methods may include administering to the subject an antibody or antibody fragment disclosed above subcutaneously at about 330 mg/month for about 3, 4, 5, 6, 7, 8, 9, 10, 11 or 12 months or longer, and the subject is an adult human. Other embodiments provide administering the antibody or antibody fragment weekly at no less than 2 mg/kg/week (166 mg for an averaged human patient of 83 kg); preferably, about 4 mg/kg/week (332 mg for an averaged human patient of 83 kg). In another aspect, the composition of an anti-oxLDL antibody is administered biweekly at >2.5 mg/kg/two weeks (e.g., 208 mg for an averaged human patient of 83 kg). In yet another aspect, the composition of an anti-oxLDL antibody is administered monthly at about 6 mg/kg/month (e.g., about 498 mg for an averaged human patient of 83 kg). For example, the monthly dosing may be carried out for 12 months or 3 months. Yet other embodiments provide administering an antibody or antibody fragment to a subject at an initial dose of 800-900 mg, 900-1000 mg, 1000-1100 mg, 1100-1200 mg, 1200-1300 mg, 1300-1400 mg, 1400-1500 mg, or 1500-1600 mg. In some aspects, the effective amount in the method described herein includes an initial dose of orticumab of approximately 1000-1500 mg, followed by subsequent doses of the antibody at 700-900 mg administered weekly for 2, 3, 4 or 5 weeks and/or even administered monthly for 1, 2 or 3 months.

Other embodiments provide administering step-wise escalating doses of the anti-oxLDL antibody or fragment. In this embodiment, an exemplary (starting) dose of a single-dose administration of an antibody (e.g., orticumab) against oxLDL is between 0.005 and 0.01 mg/kg (e.g., intravenously); and other exemplary dosage levels to be administered in the single-dose administration are between 0.01 and 0.15, between 0.15 and 0.75, between 0.75 and 2.5, between 2.5 and 7.5, and between 7.5 and 30 mg/kg (e.g., intravenously). For example, a starting dose of orticumab in a single-dose intravenous administration is 0.007 mg/kg; and other exemplary dosages can be 0.05, 0.25, 1.25, 5.0 or 15.0 mg/kg in subsequent single-dose intravenous administration. In another embodiment, a single-dose subcutaneous administration of the antibody is between 0.5 and 5 mg/kg, and a multiple-dose subcutaneous administration is also between 0.5 and 5 mg/kg. For example, the antibody at 1.25 mg/kg is administered subcutaneously. In various embodiments, the dosage is administered within a specified hour range of the day in each administration, and each dose in a multiple-dose treatment (e.g., 4 doses, 3 doses, 5 doses, or 6 doses) is administered at weekly intervals with a time window of ±1 day. In another example, an antibody (e.g., orticumab) is administered at between 300 mg and 450 mg (e.g., 360 mg) to a human subject, optionally followed by another dose between 300 mg and 450 mg (e.g., 360 mg) to the human subject where the second dose is at least 70 days (up to 91 days) apart from the first dose. The antibody may be formulated at a concentration of 100-170 mg/mL (e.g., 150 mg/mL) and for use in subcutaneous administration without further dilution or diluted to a large volume for intravenous infusion.

Further embodiments include administering to the subject an effective amount of the antibody in the range of about 10-50 µg/period, 50-100 µg/period, 100-150 µg/period, 150-200 µg/period, 100-200 µg/period, 200-300 µg/period, 300-400 µg/period, 400-500 µg/period, 500-600 µg/period, 600-700 µg/period, 700-800 µg/period, 800-900 µg/period, 900-1000 µg/period, 1000-1100 µg/period, 1100-1200 µg/period, 1200-1300 µg/period, 1300-1400 µg/period, 1400-1500 µg/period, 1500-1600 µg/period, 1600-1700 µg/period, 1700-1800 µg/period, 1800-1900 µg/period, 1900-2000 µg/period, 2000-2100 µg/period, 2100-2200 µg/period, 2200-2300 µg/period, 2300-2400 µg/period, 2400-2500 µg/period, 2500-2600 µg/period, 2600-2700 µg/period, 2700-2800 µg/period, 2800-2900 µg/period or 2900-3000 µg/period. A period is a day, a week, a month, or another length of time. One aspect is the antibody (e.g., orticumab) is administered at a weekly, biweekly or monthly frequency of any of above-mentioned dosage per period.

In some embodiments, the methods include administering the anti-oxLDL antibody (e.g., orticumab) to the subject for 1-5 days, 1-5 weeks, 1-5 months, or 1-5 years. For example, the antibody is administered to the subject in 3, 4, 5, 6, 7, 8, 9, 10, 11, 12, 13, 14, 15, 16, 17, 18, 19 or 20 doses, each dose separated by at least 3 days, 5 days, one week, two weeks, one month, two months, or a combination thereof. In other embodiments, the second dose is administered about 2-3 weeks, or about 3 weeks after the first dose and the third dose is administered about 5-6 weeks or about 6 weeks after the first dose, etc. In another embodiment, the second dose is administered about 2-3 months, about 2 months, about 3 months, or about 4 months after the first dose and the third dose is administered about 4-6 months, about 5-6 months, about 5 months, or about 6 months after the first dose.

Pharmaceutical Compositions and Medicaments

In various embodiments, the present invention provides a pharmaceutical composition for use in the methods. The pharmaceutical composition includes anti-oxLDL antibody or fragment thereof and a pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Examples of excipients include but are not limited to starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, antioxidants, plasticizers, gelling agents, thickeners, hardeners, setting agents, suspending agents, surfactants, humectants, carriers, stabilizers, and combinations thereof. Generally, each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

Antibody Preparation

The present inventions based in part on the use of anti-oxLDL antibodies, fragments, and binding proteins. Modern recombinant library technology is used to prepare therapeutic antibodies against oxLDL. While murine hybridomas cells produce large amounts of identical antibodies, these non-human antibodies are recognized by human body as foreign, and as a consequence, their efficacy and plasma half-lives are decreased in addition to eliciting allergic reactions. To solve this problem, one approach is to make chimeric antibodies where the murine variable domains of the antibody are transferred to human constant regions resulting in an antibody that is mainly human. A further refinement of this approach is to develop humanized antibodies where the regions of the murine antibody that contacted the antigen, the Complementarity Determining Regions (CDRs) are transferred to a human antibody framework, resulting in a humanized antibody. Another approach is to produce completely human antibodies using recombinant technologies, which does not rely on immunization of animals to generate the specific antibody. Instead recombinant libraries comprise a huge number of pre-made antibody variants and it is likely that a library will have at least one antibody specific for any antigen. A phage display system may be used where antibody fragments are expressed, displayed, as fusions with phage coat proteins on the surface of filamentous phage particles, while the phage display system simultaneously carries the genetic information encoding the displayed molecule. Phage displaying antibody fragments specific for a particular antigen may be selected through binding to the antigen in question. Isolated phage may then be amplified and the gene encoding the selected antibody variable domains may optionally be transferred to other antibody formats as e.g. full-length immunoglobulin and expressed in high amounts using appropriate vectors and host cells well known in the art. The format of displayed antibody specificities on phage particles may differ. The most commonly used formats are Fab and single chain (scFv) both containing the variable antigen binding domains of antibodies. The single chain format is composed of a variable heavy domain (VH) linked to a variable light domain (VL) via a flexible linker. Before use as analytical reagents, or therapeutic agents, the displayed antibody specificity is transferred to a soluble format, e.g., Fab or scFv, and analyzed as such. In later steps the antibody fragment identified to have desirable characteristics may be transferred into yet other formats such as full-length antibodies.

Antibody Production from Hybridomas

The cell fusions are accomplished by standard procedures well known to those skilled in the field of immunology. Fusion partner cell lines and methods for fusing and selecting hybridomas and screening for mAbs are well known in the art. See, e.g., Ausubel, Harlow, and Colligan, the contents of which references are incorporated entirely herein by reference.

An anti-oxLDL antibody can be produced in large quantities by injecting hybridoma or transfectoma cells secreting the antibody into the peritoneal cavity of mice and, after appropriate time, harvesting the ascites fluid which contains a high titer of the mAb, and isolating the mAb therefrom. For such in vivo production of the mAb with a non-murine hybridoma (e.g., rat or human), hybridoma cells are preferably grown in irradiated or athymic nude mice. Alternatively, the antibodies can be produced by culturing hybridoma or transfectoma cells in vitro and isolating secreted mAb from the cell culture medium or recombinantly, in eukaryotic or prokaryotic cells.

Recombinant Expression of Antibodies

Recombinant murine or chimeric murine-human or human-human antibodies that inhibit oxidized LDL can be provided according to the present invention using known techniques based on the teaching provided herein. See, e.g., Ausubel et al., eds. Current Protocols in Molecular Biology, Wiley Interscience, N.Y. (1987, 1992, 1993); and Sambrook et al. Molecular Cloning: A Laboratory Manual, Cold Spring Harbor Laboratory Press (1989).

The DNA encoding an anti-oxLDL antibody can be genomic DNA or cDNA which encodes at least one of the heavy chain constant region (Hc), the heavy chain variable region (Hc), the light chain variable region (Lv) and the light chain constant regions (Lc). A convenient alternative to the use of chromosomal gene fragments as the source of DNA encoding the murine V region antigen-binding segment is the use of cDNA for the construction of chimeric immunoglobulin genes, e.g., as reported by Liu et al. (Proc. Natl. Acad. Sci., USA 84:3439 (1987) and J. Immunology 139: 3521 (1987). The use of cDNA requires that gene expression elements appropriate for the host cell be combined with the gene in order to achieve synthesis of the desired protein. The use of cDNA sequences is advantageous over genomic sequences (which contain introns), in that cDNA sequences can be expressed in bacteria or other hosts which lack appropriate RNA splicing systems.

EXAMPLES

The following examples are not intended to limit the scope of the claims to the invention but are rather intended to be exemplary of certain embodiments. Any variations in the exemplified methods which occur to the skilled artisan are intended to fall within the scope of the present invention.

Example 1: Orticumab Specifically Binds to oxLDL

The binding specificity of orticumab for the various forms of LDL was investigated. In this experiment, the binding of orticumab to native (unoxidized) LDL and malondialdehyde-modified LDL (MDA-LDL) was measured across various concentrations of orticumab, and the dissociation constant ($K_d$) was calculated. MDA-LDL was selected for this experiment because it is an endogenous LDL species that is believed to reflect the naturally-occurring levels of oxLDL.

Orticumab was tested in an ELISA assay for binding to malondialdehyde (MDA)-modified and native human LDL prepared from the sera of blood donors. LDL samples were immobilized on the plate and the antibody concentration was titrated. A multi-well plate was coated with 50 µl MDA-LDL or native LDL per well and diluted to 2 ug/mL with PBS+1 mM EDTA. The plate was incubated overnight at 4° C. Purified antibody was dilute, titrated in ELISA block buffer (0.2% non-fat dry milk), and applied. The plate was incubated for 1 hour at room temperature. Bound antibody was detected with the horseradish peroxidase (HRP)-conjugated rabbit anti-human IgG antibody (P0214 DAKO).

FIG. 1 provides exemplary binding curves from of orticumab (0.01-50 µg/ml) for native LDL and MDA-LDL. Orticumab lacked any significant affinity for native LDL but demonstrated robust and specific binding of MDA-LDL with a $K_d$ of about 8±6 nM.

Example 2: Orticumab Blocks oxLDL-Induced Release of MCP-1 by Macrophages

The effect of orticumab on the oxLDL-induced release of MCP-1 by macrophages was measured in order to assess potential anti-inflammatory effects. MCP-1 is a macrophage chemoattractant that is secreted by activated macrophages in areas of inflammation and serves to enhance the inflammatory response. MCP-1 expression correlates with tumor-associated macrophage infiltration.

Figure 2A:
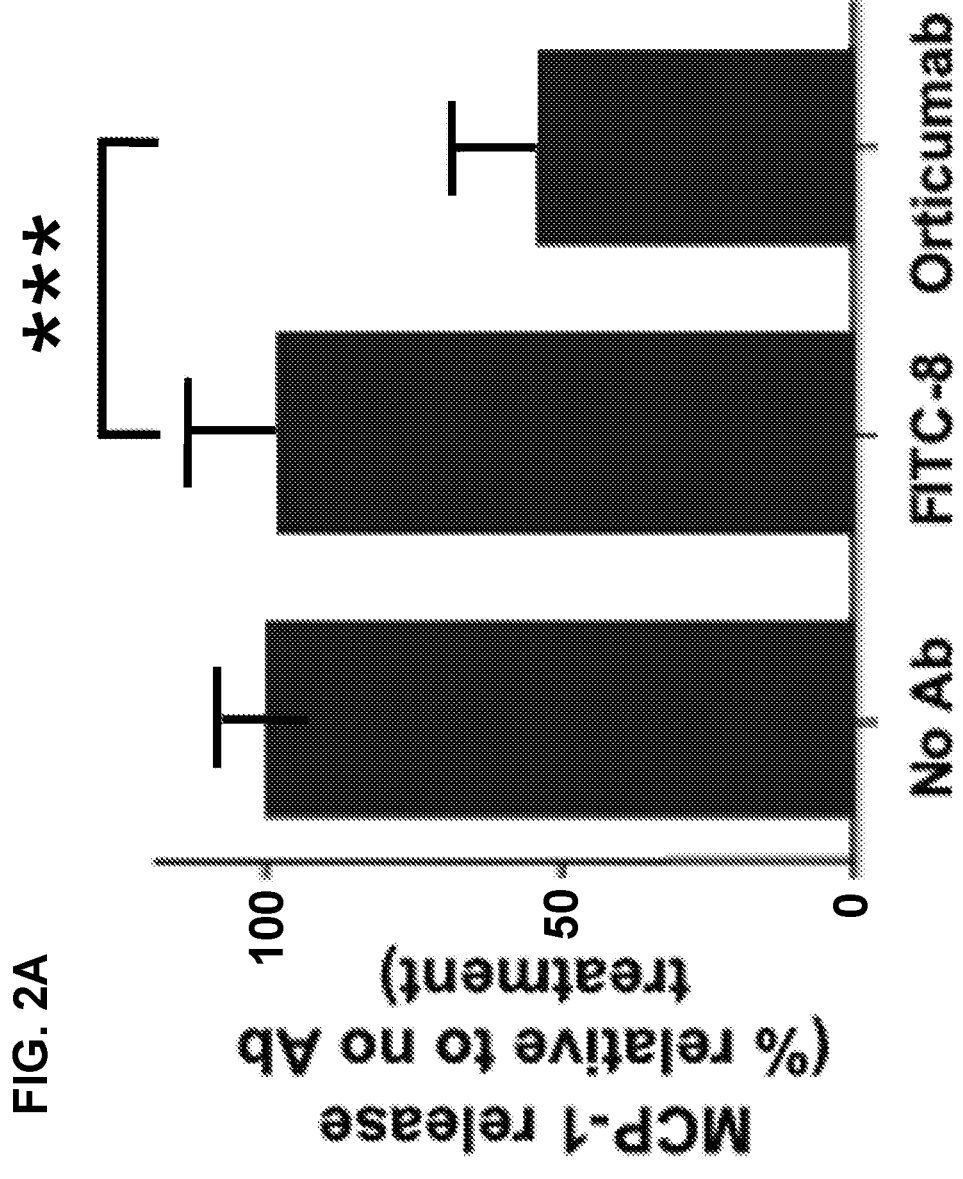
FIG. 2A is a bar graph showing the MCP-1 release from cells treated with orticumab and a control antibody.

Freshly isolated CD14+ macrophages were pre-activated with 0.1 ng/mL lipopolysaccharide (LPS) to generate proinflammatory M1 macrophages. After 20 hours of pre-activation, orticumab, FITC-8, or an equal volume of medium were added to a final concentration of 40 nM and the cells were cultured for an additional 24 hours. Culture supernatants were collected and analyzed for MCP-1 levels using a cytometric bead array (CBA; BD Bioscience, Franklin Lakes, NJ, USA). FIG. 2A shows mean values (+/−SD) or pooled and normalized data obtained from two different donors in two different experiments with treatments performed in triplicate. Values were normalized against mean MCP-1 values of samples receiving no antibody treatment. Statistical analysis was performed by ANOVA—followed by Tukey-Kramer's multiple comparison test using Graph-Pad Instat 3 software (***$p<0.001$). (Data on file; report BI 209-68) The results demonstrate that orticumab treatment significantly reduced MCP-1 secretion in ox-LDL-stimulated macrophages relative to treatment with a control antibody (FITC-8) and vehicle control ("no Ab").

Figure 2B:
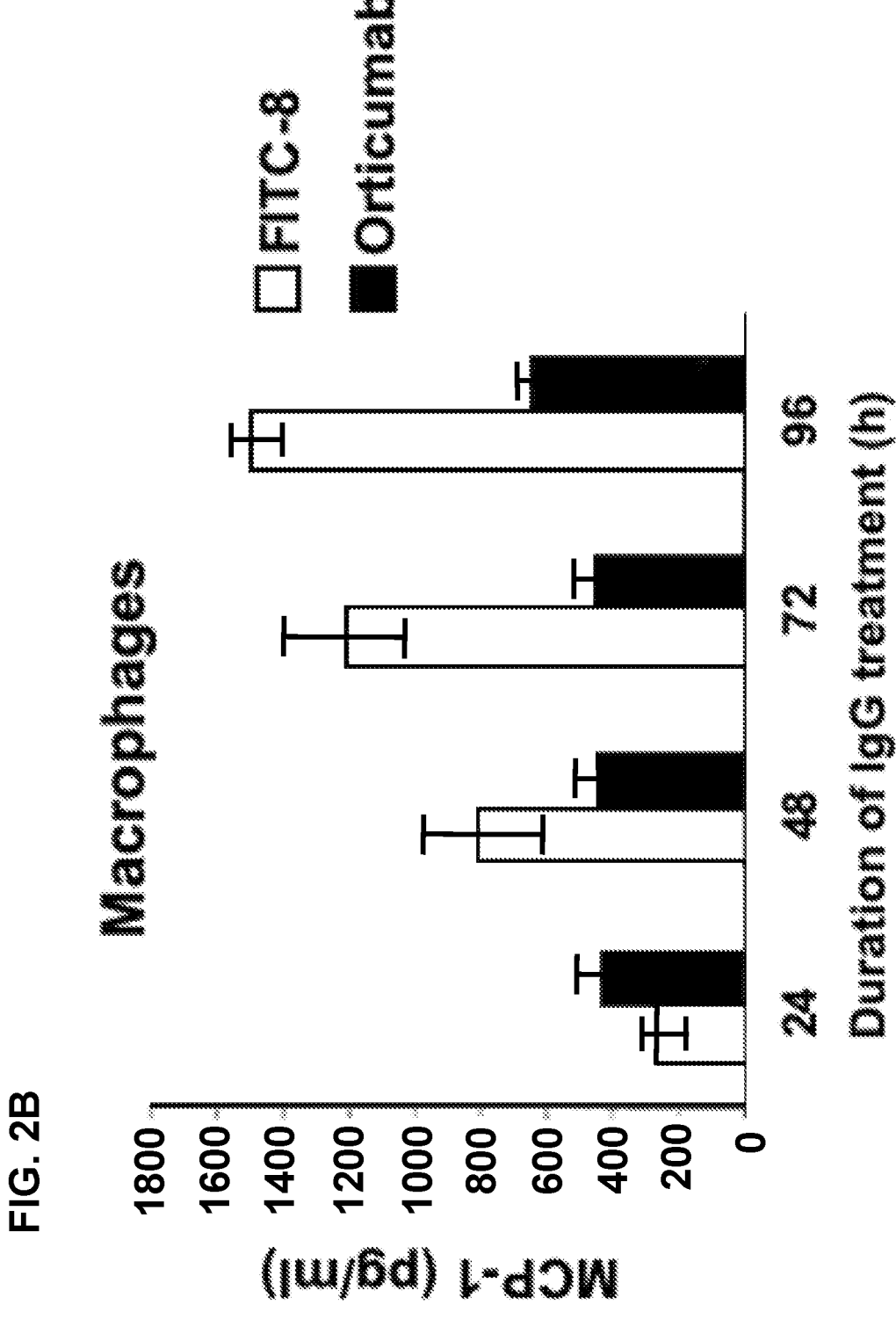
FIG. 2B is a bar graph showing the accumulated MCP-1 release over time.

In another experiment, human monocyte derived macrophages were grown for 14 days in the presence of oxLDL-containing human serum. These cells were then treated with control IgG (FITC-8) or orticumab for the indicated time periods. Supernatants were removed each day and analyzed for MCP-1 levels. FIG. 2B illustrates that, in the presence of orticumab, MCP-1 levels did not increase over time as was observed in cultures treated with the control antibody indicating that orticumab effectively blocked MCP-1 secretion. For example, After the 4 days (96 hours), orticumab blocked the increase in MCP-1 decreased macrophage MCP-1 release by up to 60% compared to cells treated with control IgG.

Example 3: Orticumab Inhibits NFκB Signaling by Increasing IκBα Expression

NFκB is a well-known transcriptional regulator that responds to stressful stimuli in most cell types and generally upregulates the immune response and genes involved in inflammation. In unstimulated cells, NFκB is primarily cytoplasmic and sequestered by inhibitors including the IκBs which mask its nuclear localization signal. Upon cellular stimulation, the IκBs are rapidly phosphorylated by IκB kinase ("IKK") and subsequently ubiquitinated and degraded. Once freed from IκB inhibition, NFκB rapidly translocates to the nucleus.

The effect of orticumab on oxLDL signaling was investigated in the NFκB pathway. Macrophages were stimulated with lipopolysaccharide (LPS) in the presence of oxLDL and treated with either orticumab or a mutant orticumab-like antibody that lacks significant affinity for oxLDL and/or native LDL. Monocytes were isolated from healthy subjects and incubated in the absence or presence of 0.3 ng/mL lipopolysaccharide (LPS). Cells were concurrently treated with control antibody, orticumab, or mutant orticumab. Cells were then harvested and immunoblotted for total amount of total IκBa or control protein (actin). Whole-cell lysates from primary human monocytes were extracted with RIPA buffer (150 mM NaCl, 1.0% IGEPAL CA-630, 0.5% v/v sodium deoxycholate, 0.1% w/v SDS, and 50 mM Tris-chloride, pH 8.0). After centrifugation to remove cell debris, aliquots of the 20,000 g supernatant were subjected to 10% SDS/PAGE, after which the proteins were transferred to Hybond-C extra nitrocellulose filters (Amersham Biosciences, Piscataway, NJ). The filters were incubated at room temperature with primary antibodies. Bound antibodies were visualized by chemiluminescence (Super Signal Substrate; Thermo Fisher Scientific, Waltham, MA) using a 1:5000 dilution of donkey anti-rabbit IgG, or donkey anti-mouse IgG (Jackson ImmunoResearch, West Grove, PA), conjugated to horseradish peroxidase. Filters were exposed to Kodak X-Omat BlueXB-1 film at room temperature for 1-60 s.

Figure 3:
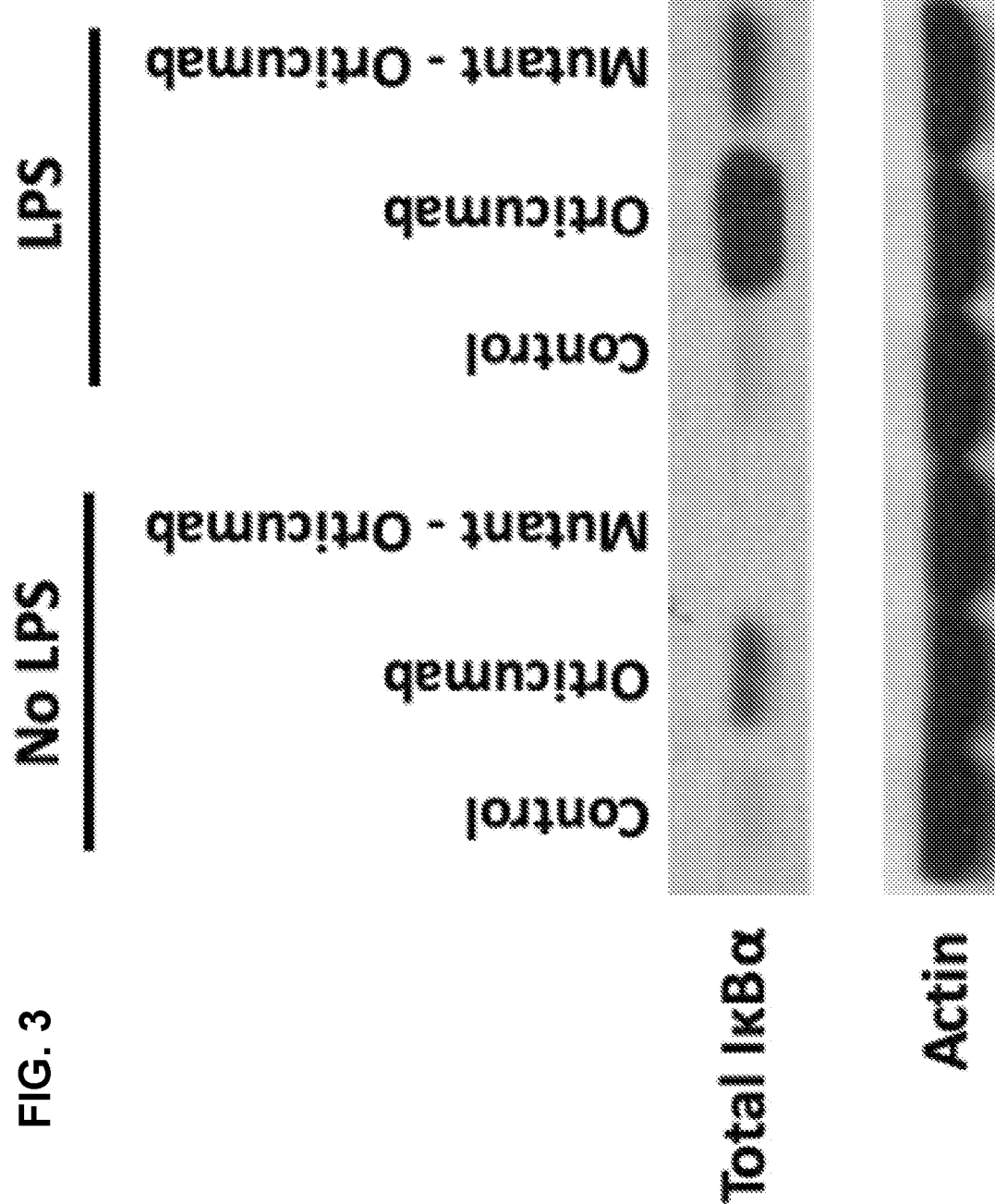
FIG. 3 is a photomicrograph of a western blot stained for IκBα.

As shown in FIG. 3, it was discovered that orticumab treatment induces the expression of IκBα in both LPS-stimulated and control macrophages. These results suggest that orticumab has anti-inflammatory activity in oxLDL-stimulated macrophages by inhibiting NFκB via increased IκBa expression.

Example 4: Orticumab Inhibits Macrophage Infiltration

Based on the foregoing biochemical evidence, the ultimate effect of orticumab on oxLDL-induced macrophage infiltration was investigated. A well-characterized murine model of atherosclerosis was used. Apobec-1–/–/LDLR–/– mice with C57BL/6 background from Jackson Laboratories (Bar Harbor, Maine), which express full-length apoB-100 in their LDL particles and have a 3-fold higher plasma levels of apoB-100 than LDLR–/– mice were fed a high-cholesterol diet (15% cholesterol, 21% fat; Lactamin AB, Kimstad Sweden) provided ad libitum starting at 4 weeks of age. One week before the first treatment (24 weeks of age), the diet was changed to normal chow. One week later (at 25 weeks of age), one group of mice was sacrificed as a baseline control (Baseline 25w). The remaining animals were left untreated (Control 29w) or administered 1 mg (0.5 mL) of control IgG antibody (fluorescein isothiocyanate-8 (FITC-8) or orticumab via intraperitoneal (IP) injection. The injections were repeated at weekly intervals for a total of 3 doses, and the mice were sacrificed 2 weeks after the last injection (29 weeks of age).

Figure 4A:
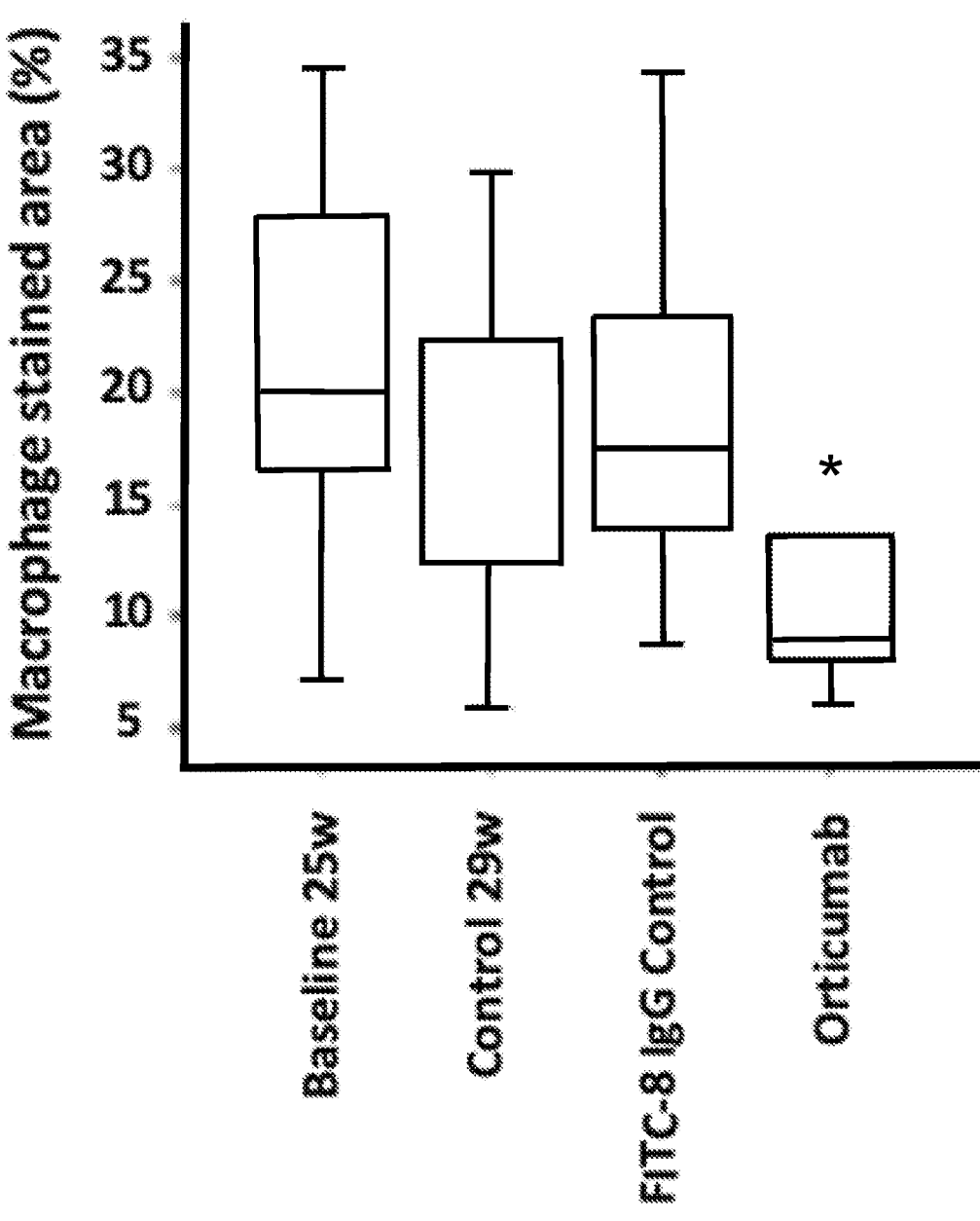
FIGS. 4A-4B are graphs showing the macrophage infiltration (FIG. 4A) and total plaque burden (FIG. 4B) in a murine model of atherosclerosis following treatment with orticumab or control antibody.
Figure 4B:
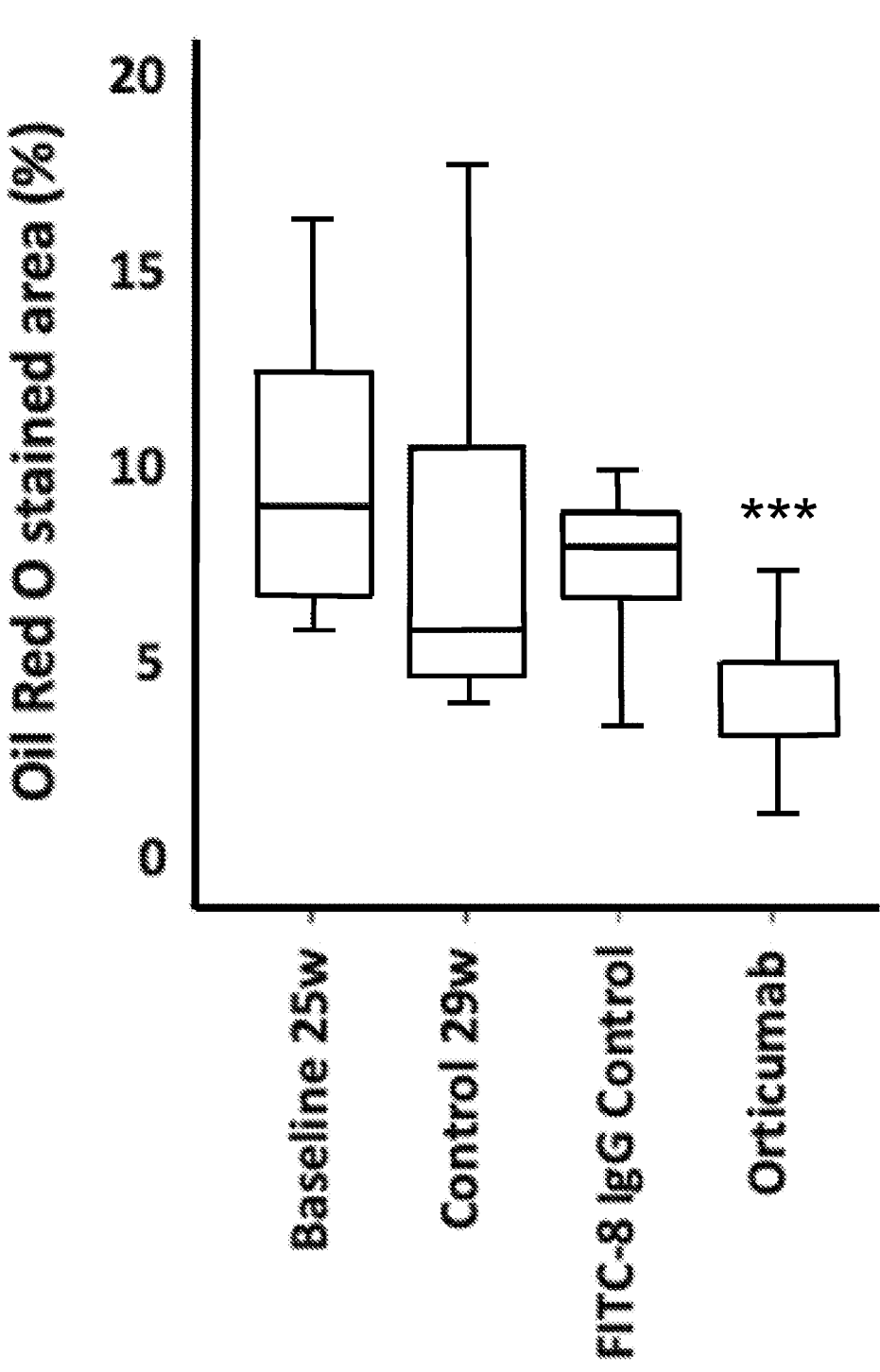

The efficacy of orticumab for limiting macrophage infiltration was assessed using two endpoints. FIG. 4A demonstrates that orticumab treatment for four weeks after plaque formation significantly reduced the observed number infiltrating macrophages relative to controls that were either untreated or administered a control IgG. This inhibition resulted in beneficial physiological changes in the treated subjects. Macrophage infiltration was assessed in the innominate artery via MOMA2 monoclonal antibody staining (*p<0.05 vs FITC-8). FIG. 4B illustrates that orticumab treatment significantly reduced the plaque burden relative to the pre-treatment condition and the various controls. Plaque burden was assessed in the descending aorta by Oil Red 0 staining and calculating the percentage of total plaque area per total area of the descending aorta. P-values were calculated versus fluorescein isothiocyanate-8 (FITC-8) (***p<0.001 vs FITC-8).

All references cited herein are incorporated by reference in their entirety as though fully set forth. Unless defined otherwise, technical and scientific terms used herein have the same meaning as commonly understood by one of ordinary skill in the art to which this invention belongs. Allen et al., Remington: The Science and Practice of Pharmacy 22nd ed., Pharmaceutical Press (Sep. 15, 2012); Hornyak et al., Introduction to Nanoscience and Nanotechnology, CRC Press (2008); Singleton and Sainsbury, Dictionary of Microbiology and Molecular Biology 3rd ed., revised ed., J. Wiley & Sons (New York, N.Y. 2006); Smith, March's Advanced Organic Chemistry Reactions, Mechanisms and Structure 7th ed., J. Wiley & Sons (New York, N.Y. 2013); Singleton, Dictionary of DNA and Genome Technology 3rd ed., Wiley-Blackwell (Nov. 28, 2012); and Green and Sambrook, Molecular Cloning: A Laboratory Manual 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, Antibodies A Laboratory Manual 2nd ed., Cold Spring Harbor Press (Cold Spring Harbor N.Y., 2013); Köhler and Milstein, Derivation of specific antibody-producing tissue culture and tumor lines by cell fusion, Eur. J. Immunol. 1976 Jul. 6(7):511-9; Queen and Selick, Humanized immunoglobulins, U.S. Pat. No. 5,585,089 (1996 December); and Riechmann et al., Reshaping human antibodies for therapy, Nature 1988 Mar. 24, 332(6162):21-7.

The foregoing description sets forth the invention and method of use in several embodiments. Those having ordinary skill in the art may be able to make alterations and modifications to what is described herein without departing from its spirit and scope. While this invention is susceptible to different embodiments in different forms, there is shown in the drawings and will herein be described in detail a preferred embodiment of the invention with the understanding that the present disclosure is to be considered as an exemplification of the principles of the invention and is not intended to limit the broad aspect of the invention to the embodiment illustrated. All features, elements, components, functions, and steps described with respect to any embodiment provided herein are intended to be freely combinable and substitutable with those from any other embodiment unless otherwise stated. Therefore, it should be understood that what is illustrated is set forth only for the purposes of example and should not be taken as a limitation on the scope of the present invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

The invention claimed is:

1. A method for inhibiting macrophage infiltration into a tumor in a subject comprising administering to the subject a therapeutically effective amount of an antibody or fragment thereof that binds to oxidized low density lipoprotein (oxLDL), wherein the antibody or fragment thereof comprises heavy chain complementarity determining regions (HCDRs) of SEQ ID NO: 5, SEQ ID NO: 6, and SEQ ID NO: 7 and light chain complementarity determining regions (LCDRs) of SEQ ID NO: 8, SEQ ID NO: 9, and SEQ ID NO: 10.

2. The method of claim 1, wherein the tumor is LOX-1-positive.

3. The method of claim 1, wherein the tumor is a CD36-positive tumor.

4. The method of claim 1, wherein the tumor is selected from the group consisting of ovarian carcinoma, bladder urothelial carcinoma, kidney renal clear cell carcinoma, rectum adenocarcinoma, colon adenocarcinoma, prostate adenocarcinoma, a mammary epithelial cell tumor, a glioblastoma, pancreatic cancer, and esophageal cancer.

5. The method of claim 1, wherein the method reduces growth rate of the tumor.

6. A method for inhibiting metastasis of a tumor in a subject comprising administering to the subject a therapeutically effective amount of an antibody or fragment thereof that binds to oxidized low density lipoprotein (oxLDL), wherein the antibody or fragment thereof comprises heavy chain complementarity determining regions (HCDRs) of SEQ ID NO: 5, SEQ ID NO: 6, and SEQ ID NO: 7 and light chain complementarity determining regions (LCDRs) of SEQ ID NO: 8, SEQ ID NO: 9, and SEQ ID NO: 10.

7. A method for treating a cancer in a subject comprising administering to the subject a therapeutically effective amount of an antibody or fragment thereof that binds to oxidized low density lipoprotein (oxLDL), wherein the antibody or fragment thereof comprises heavy chain complementarity determining regions (HCDRs) of SEQ ID NO: 5, SEQ ID NO: 6, and SEQ ID NO: 7 and light chain complementarity determining regions (LCDRs) of SEQ ID NO: 8, SEQ ID NO: 9, and SEQ ID NO: 10.

8. The method of claim 7, wherein the method further comprises administering to the subject a therapeutically effective amount of a primary anticancer therapy selected from the group consisting of a chemotherapy, radiation therapy, and immunotherapy.

9. The method of claim 7, wherein the cancer is LOX-1-positive.

10. The method of claim 7, wherein the cancer is a CD36-positive tumor.

11. The method of claim 7, wherein the cancer is selected from the group consisting of ovarian carcinoma, bladder urothelial carcinoma, kidney renal clear cell carcinoma, rectum adenocarcinoma, colon adenocarcinoma, prostate adenocarcinoma, a mammary epithelial cell tumor, a glioblastoma, pancreatic cancer, and esophageal cancer.

12. The method of claim 7, wherein the cancer is a hematological cancer.

13. The method of claim 7, wherein the subject is diagnosed as having serum hyperlipidemia, type 2 diabetes, or metabolic syndrome.

14. The method of claim 7, wherein the antibody or fragment thereof comprises a variable heavy region (VH) of SEQ ID NO: 11, a variable light region (VL) of SEQ ID NO: 12, or both.

15. The method of claim 7, wherein the antibody or fragment thereof comprises a heavy chain of SEQ ID NO: 3, a light chain of SEQ ID NO: 4, or both.

16. The method of claim 7, wherein the antibody is orticumab.

17. The method of claim 7, wherein the antibody or fragment thereof is administered intravenously at an initial dose of at least 5 mg/kg, followed by a plurality of subsequent doses, each at least 2 mg/kg/week, at least 2.5 mg/kg/two weeks, or at least 6 mg/kg/month.

18. The method of claim 7, wherein the antibody or fragment thereof is administered subcutaneously at a dose of about 330 mg/month for at least three months.

* * * * *

SEQUENCE LISTING

<160> NUMBER OF SEQ ID NOS: 12

<210> SEQ ID NO 1
<211> LENGTH: 1353
<212> TYPE: DNA
<213> ORGANISM: Artificial Sequence
<220> FEATURE:
<223> OTHER INFORMATION: Polynucleotide sequence encoding heavy chain of
      oxLDL-specific antibody

<400> SEQUENCE: 1

```
gaggtgcagc tgttggagtc tggggggaggc ttggtacagc ctgggggggtc cctgagactc        60 tcctgtgcag cctctggatt caccttcagt aacgcctgga tgagctgggt ccgccaggct       120
ccagggaagg ggctggagtg ggtctcaagt attagtgttg gtggacatag gacatattat       180
gcagattccg tgaagggccg gtccaccatc tccagagaca attccaagaa cacgctgtat       240
ctgcaaatga acagcctgag agccgaggac actgccgtgt attactgtgc acggatacgg       300
gtgggtccgt ccggcggggc ctttgactac tggggccagg gtacactggt caccgtgagc       360
tcagcctcca ccaagggccc atcggtcttc cccctggcac cctcctccaa gagcacctct       420
gggggcacag cggccctggg ctgcctggtc aaggactact tccccgaacc ggtgacggtg       480
tcgtggaact caggcgccct gaccagcggc gtgcacacct tcccggctgt cctacagtcc       540
tcaggactct actccctcag cagcgtggtg accgtgccct ccagcagctt gggcacccag       600
acctacatct gcaacgtgaa tcacaagccc agcaacacca aggtggacaa gaaagttgag       660
cccaaatctt gtgacaaaac tcacacatgc ccaccgtgcc cagcacctga actcctgggg       720
ggaccgtcag tcttcctctt ccccccaaaa cccaaggaca ccctcatgat ctcccggacc       780
cctgaggtca catgcgtggt ggtggacgtg agccacgaag accctgaggt caagttcaac       840
tggtacgtgg acggcgtgga ggtgcataat gccaagacaa agccgcggga ggagcagtac       900
aacagcacgt accgtgtggt cagcgtcctc accgtcctgc accaggactg gctgaatggc       960
aaggagtaca agtgcaaggt ctccaacaaa gccctcccag cccccatcga gaaaaccatc      1020
tccaaagcca aagggcagcc ccgagaacca caggtgtaca ccctgccccc atcccgggat      1080
gagctgacca gaaccaggt cagcctgacc tgcctggtca aaggcttcta tcccagcgac      1140
atcgccgtgg agtgggagag caatgggcag ccggagaaca actacaagac cacgcctccc      1200
gtgctggact ccgacggctc cttcttcctc tacagcaagc tcaccgtgga caagagcagg      1260
tggcagcagg ggaacgtctt ctcatgctcc gtgatgcatg aggctctgca caaccactac      1320
acgcagaaga gcctctccct gtctccgggt aaa                                   1353
```

<210> SEQ ID NO 2
<211> LENGTH: 648
<212> TYPE: DNA
<213> ORGANISM: Artificial Sequence
<220> FEATURE:
<223> OTHER INFORMATION: Polynucleotide sequence encoding light chain of
      oxLDL-specific antibody

<400> SEQUENCE: 2

```
cagtctgtgc tgactcagcc accctcagcg tctgggaccc ccgggcagag ggtcaccatc        60
tcctgctctg gaagcaacac caacattggg aagaactatg tatcttggta tcagcagctc       120
ccaggaacgg cccccaaact cctcatctat gctaatagca atcggccctc aggggtccct       180
gaccgattct ctggctccaa gtctggcacc tcagcctccc tggccatcag tgggctccgg       240
tccgaggatg aggctgatta ttactgtgcg tcatgggatg ccagcctgaa tggttgggta       300
```

```
ttcggcggag gaaccaagct gacggtccta ggtcagccca aggctgcccc ctcggtcact    360
ctgttcccgc cctcctctga ggagcttcaa gccaacaagg ccacactggt gtgtctcata    420
agtgacttct acccgggagc cgtgacagtg gcctggaagg cagatagcag ccccgtcaag    480
gcgggagtgg agaccaccac accctccaaa caaagcaaca caagtacgc ggccagcagc    540 tatctgagcc tgacgcctga gcagtggaag tcccacagaa gctacagctg ccaggtcacg    600
catgaaggga gcaccgtgga gaagacagtg gccctacag aatgttca              648
```

```
<210> SEQ ID NO 3
<211> LENGTH: 451
<212> TYPE: PRT
<213> ORGANISM: Artificial Sequence
<220> FEATURE:
<223> OTHER INFORMATION: Heavy chain

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ser Ser Ile Ser Val Gly Gly His Arg Thr Tyr Tyr Ala Asp Ser Val
    50                  55                  60

Lys Gly Arg Ser Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Arg Val Gly Pro Ser Gly Gly Ala Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300
```

```
Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 4
<211> LENGTH: 216
<212> TYPE: PRT
<213> ORGANISM: Artificial Sequence
<220> FEATURE:
<223> OTHER INFORMATION: Light chain

<400> SEQUENCE: 4

Gln Ser Val Leu Thr Gln Pro Pro Ser Ala Ser Gly Thr Pro Gly Gln
1               5                   10                  15

Arg Val Thr Ile Ser Cys Ser Gly Ser Asn Thr Asn Ile Gly Lys Asn
                20                  25                  30

Tyr Val Ser Trp Tyr Gln Gln Leu Pro Gly Thr Ala Pro Lys Leu Leu
            35                  40                  45

Ile Tyr Ala Asn Ser Asn Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ser Trp Asp Ala Ser Leu
                85                  90                  95

Asn Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205
```

-continued

```
Thr Val Ala Pro Thr Glu Cys Ser
    210                 215

<210> SEQ ID NO 5
<211> LENGTH: 14
<212> TYPE: PRT
<213> ORGANISM: Artificial Sequence
<220> FEATURE:
<223> OTHER INFORMATION: HCDR1

<400> SEQUENCE: 5

Phe Ser Asn Ala Trp Met Ser Trp Val Arg Gln Ala Pro Gly
1               5                   10

<210> SEQ ID NO 6
<211> LENGTH: 19
<212> TYPE: PRT
<213> ORGANISM: Artificial Sequence
<220> FEATURE:
<223> OTHER INFORMATION: HCDR2

<400> SEQUENCE: 6

Ser Ser Ile Ser Val Gly Gly His Arg Thr Tyr Tyr Ala Asp Ser Val
1               5                   10                  15

Lys Gly Arg

<210> SEQ ID NO 7
<211> LENGTH: 14
<212> TYPE: PRT
<213> ORGANISM: Artificial Sequence
<220> FEATURE:
<223> OTHER INFORMATION: HCDR3

<400> SEQUENCE: 7

Ala Arg Ile Arg Val Gly Pro Ser Gly Gly Ala Phe Asp Tyr
1               5                   10

<210> SEQ ID NO 8
<211> LENGTH: 14
<212> TYPE: PRT
<213> ORGANISM: Artificial Sequence
<220> FEATURE:
<223> OTHER INFORMATION: LCDR1

<400> SEQUENCE: 8

Cys Ser Gly Ser Asn Thr Asn Ile Gly Lys Asn Tyr Val Ser
1               5                   10

<210> SEQ ID NO 9
<211> LENGTH: 7
<212> TYPE: PRT
<213> ORGANISM: Artificial Sequence
<220> FEATURE:
<223> OTHER INFORMATION: LCDR2

<400> SEQUENCE: 9

Ala Asn Ser Asn Arg Pro Ser
1               5

<210> SEQ ID NO 10
<211> LENGTH: 12
<212> TYPE: PRT
<213> ORGANISM: Artificial Sequence
<220> FEATURE:
<223> OTHER INFORMATION: LCDR3
```

```
<400> SEQUENCE: 10

Cys Ala Ser Trp Asp Ala Ser Leu Asn Gly Trp Val
1               5                   10

<210> SEQ ID NO 11
<211> LENGTH: 120
<212> TYPE: PRT
<213> ORGANISM: Artificial Sequence
<220> FEATURE:
<223> OTHER INFORMATION: Variable heavy region

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ser Ser Ile Ser Val Gly Gly His Arg Thr Tyr Tyr Ala Asp Ser Val
    50                  55                  60

Lys Gly Arg Ser Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Arg Val Gly Pro Ser Gly Gly Ala Phe Asp Tyr Trp Gly
            100                 105                 110

Gln Gly Thr Leu Val Thr Val Ser
        115                 120

<210> SEQ ID NO 12
<211> LENGTH: 110
<212> TYPE: PRT
<213> ORGANISM: Artificial Sequence
<220> FEATURE:
<223> OTHER INFORMATION: Variable light region

<400> SEQUENCE: 12

Gln Ser Val Leu Thr Gln Pro Pro Ser Ala Ser Gly Thr Pro Gly Gln
1               5                   10                  15

Arg Val Thr Ile Ser Cys Ser Gly Ser Asn Thr Asn Ile Gly Lys Asn
            20                  25                  30

Tyr Val Ser Trp Tyr Gln Gln Leu Pro Gly Thr Ala Pro Lys Leu Leu
        35                  40                  45

Ile Tyr Ala Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ser Trp Asp Ala Ser Leu
                85                  90                  95

Asn Gly Trp Val Phe Gly Gly Gly Thr Lys Leu Thr Val Leu
            100                 105                 110
```